(12) United States Patent
Hsieh et al.

(10) Patent No.: US 10,928,383 B2
(45) Date of Patent: Feb. 23, 2021

(54) METHOD FOR PREDICTING EFFECT OF DRUG

(71) Applicant: Shanxi Pishon Biomedical Technology Co., LTD, Jincheng (CN)

(72) Inventors: Chih-Chiang Hsieh, Taipei (TW); Yen Chang, Taipei (TW)

(73) Assignee: SHANXI PISHON BIOMEDICAL TECHNOLOGY CO., LTD, Jincheng (CN)

(*) Notice: Subject to any disclaimer, the term of this patent is extended or adjusted under 35 U.S.C. 154(b) by 286 days.

(21) Appl. No.: 15/995,086

(22) Filed: May 31, 2018

(65) Prior Publication Data

US 2018/0348204 A1    Dec. 6, 2018

Related U.S. Application Data

(60) Provisional application No. 62/514,787, filed on Jun. 3, 2017.

(51) Int. Cl.

| | | |
|---|---|---|
| *C12N 11/12* | (2006.01) | |
| *G01N 33/48* | (2006.01) | |
| *G01N 33/50* | (2006.01) | |
| *C12N 5/071* | (2010.01) | |
| *C12N 5/00* | (2006.01) | |
| *A61K 31/505* | (2006.01) | |
| *A61K 33/24* | (2019.01) | |

(52) U.S. Cl.
CPC ....... *G01N 33/5011* (2013.01); *C12N 5/0062* (2013.01); *C12N 5/0093* (2013.01); *C12N 5/0677* (2013.01); *G01N 33/5082* (2013.01); *A61K 31/505* (2013.01); *A61K 33/24* (2013.01); *C12N 2503/02* (2013.01); *C12N 2533/78* (2013.01); *G01N 33/5091* (2013.01); *G01N 2800/52* (2013.01)

(58) Field of Classification Search
CPC ....... C08J 3/28; C08J 2301/28; C12N 5/0677; C12N 2533/78; G01N 33/5011

USPC .............................................. 435/40.51, 179
See application file for complete search history.

(56) References Cited

U.S. PATENT DOCUMENTS 3,493,651 A * 2/1970 Sloane ................. C12N 5/0068
                                                                435/235.1
2011/0159272 A1    6/2011 Yue et al.

OTHER PUBLICATIONS

Hirt et al., 2015, Biomaterials, vol. 62, p. 138-146.*
Wen, Sheng-Tung, 2018, US 20180072855 A1, effective filing date, Sep. 12, 2016.*
InvitroCue, "3D Cell Culture Platforms and Services", Dec. 8, 2016, https://invitrocue.com/wp-content/uploads/2016/12/InvitroCue_Brochure_cell_based_single_pages.pdf.
Chantal Pauli et al., Personalized In Vitro and In Vivo Cancer Models to Guide Precision Medicine, Cancer Discov. May 2017; 7(5): 462-477. doi:10.1158/2159-8290.CD-16-1154.

* cited by examiner

*Primary Examiner* — Shin Lin Chen
(74) *Attorney, Agent, or Firm* — Hannah Tien

(57) ABSTRACT

A method for predicting an effect of a medication or a treatment regimen to a subject suffering from a cancer, the method comprises: (A) obtaining a tissue from the subject; (B) dissociating the tissue to obtain a multicellular cluster, wherein the multicellular cluster comprises the cancer cell; (C) culturing the multicellular cluster on a cellulose sponge; (D) exposing the cultured multicellular cluster to the medication or the treatment regimen; and (E) measuring a first survival rate of the cancer cell before exposing to the medication or the treatment regimen and a second survival rate of the cancer cell after exposing to the medication or the treatment regimen, when the second survival rate is lower than the first survival rate, the method predicts positive effect of the medication or the treatment regimen to the subject.

6 Claims, 5 Drawing Sheets

Figure 3A    P1                                    P2
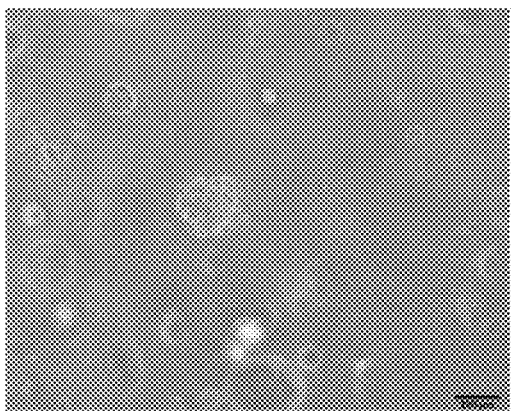 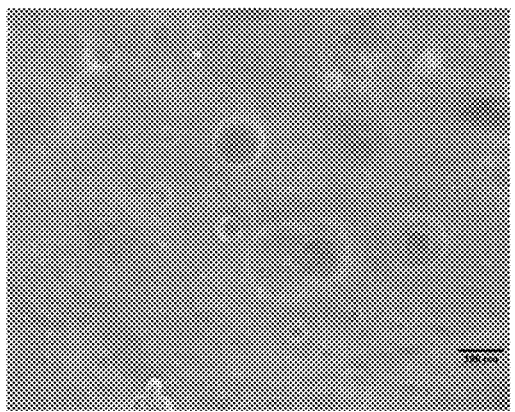
Figure 3B    P1                                    P2
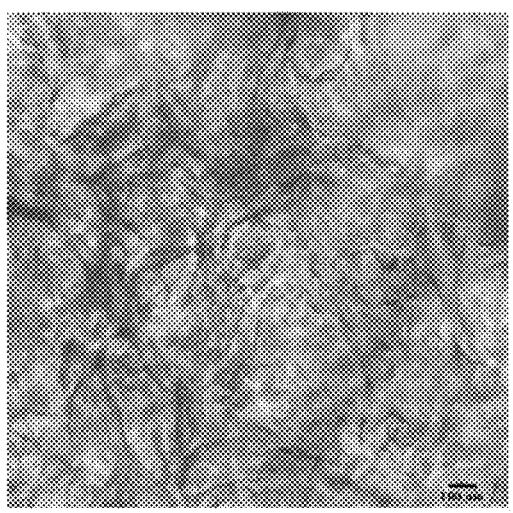 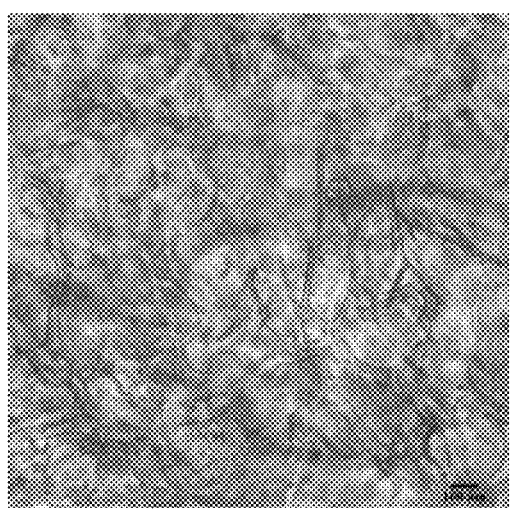

Figure 4
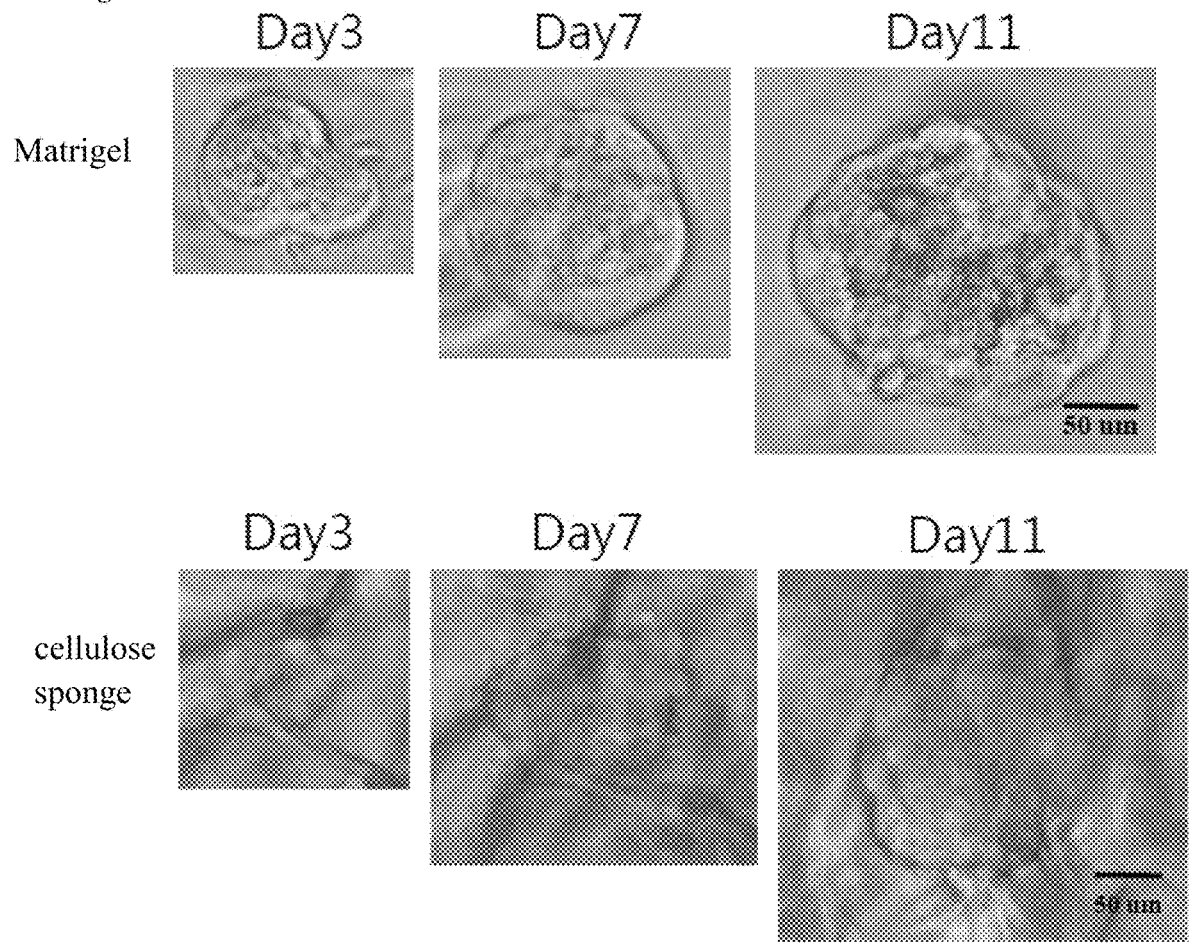
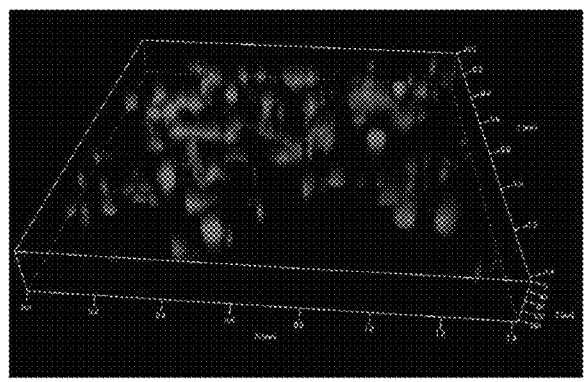
Figure 5A
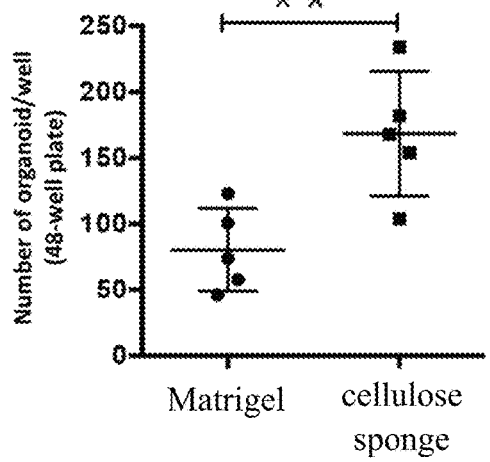
Figure 5B

METHOD FOR PREDICTING EFFECT OF DRUG

CROSS-REFERENCES TO RELATED APPLICATIONS

The present application claims priority to U.S. Provisional Appl. No. 62/514,787, filed Jun. 3, 2017 which is incorporated herein by reference in its entirety.

FIELD OF THE INVENTION

The present invention relates to a method for predicting an effect of a medication or a treatment regimen to a subject suffering from a cancer.

BACKGROUND OF THE INVENTION

The variability of individual responses to medications can complicate the treatment of many disorders. Even within a population that is relatively homogenous (i.e., same sex, a narrow range of ages, etc.), some subjects will respond well to a particular medication, while other subjects will respond poorly.

Prediction of chemotherapy response before application to the patients may improve response to chemotherapy and reduce toxicity and the cost of care, providing tailored treatment to individual patients. Chemosensitivity assays refer to any in vitro laboratory analysis that are performed specifically to evaluate whether tumor growth is inhibited by a known chemotherapy medication. Ideal in vitro chemosensitivity testing should be reproducible, feasible with small amount of tissue, and the result should be available fast with high accuracy in predicting clinical response. Various chemosensitivity and resistance assays have been developed but few have gained enough evidence to be utilized in clinical practice due to poor success rate, ambiguous criteria for defining in vitro sensitivity, prolonged turn-around time and lack of trials comparing assay-guided therapy versus empirical therapy.

In the field of biological cells, it is generally believed that the biomimetic activity of a three-dimensional culture is better than that of a two-dimensional monolayer culture. A number of three-dimensional cell culture methods have thus developed, such as a Matrigel, a hydrogel, a suspension, a hanging drop culture, a micromass culture, and a non-adherent substrate. In the field of cell culture, in order for the cultured cells to grow into tissues or organs with desired functions and forms, the use of scaffolds plays an important role. The function of the scaffold is to provide a three-dimensional framework suitable for cell growth, which is commonly known as a three-dimensional scaffold. It has a large number of pores for cell attachments or inoculations, guiding the cells to grow and differentiate in three-dimensional directions as planned to produce simulated and regenerated tissues or organs.

In traditional flat cell culture, there is only a very small area of contact between cells, half of the surface area of a cell is in contact with the culture plate, and the other half is in contact with the culture medium. A three-dimensional culture environment provides other advantages, it is capable of: providing better biochemical signals to direct cell functions, allowing cell migration within the scaffold, increasing cell density and increasing signal transmission among cells, providing molecules for cell attachments and for inducing cell differentiation. When the pore size of a sponge-like three-dimensional scaffold is greater than 50 µm, cell migration is enhanced and more uniform distribution of seeded cells and nutrients are facilitated by the inter-connecting porous structure.

Accordingly, there is a need in the art for a method of predicting the responsiveness of a subject to a particular medication or treatment regimen. A method for predicting responsiveness would allow physicians and other medical professionals to quickly determine an effective medication or treatment regimen for a particular subject, thus reducing the subject's suffering and expense. A method for predicting responsiveness would also reduce or eliminate a subject's exposure to medications or treatment regimens that are not effective, thereby reducing or eliminating suffering from side effects of such ineffective medications or treatment regimens.

SUMMARY OF THE INVENTION

The present invention provides a method for predicting an effect of a medication or a treatment regimen to a subject suffering from a cancer, the method comprises: (A) obtaining a tissue from the subject; (B) dissociating the tissue to obtain a multicellular cluster, wherein the multicellular cluster comprises the cancer cell; (C) culturing the multicellular cluster on a cellulose sponge; (D) exposing the cultured multicellular cluster to the medication or the treatment regimen; and (E) measuring a first survival rate of the cancer cell before exposing to the medication or the treatment regimen and a second survival rate of the cancer cell after exposing to the medication or the treatment regimen, when the second survival rate is lower than the first survival rate, the method predicts positive effect of the medication or the treatment regimen to the subject.

BRIEF DESCRIPTION OF THE DRAWINGS

FIG. 3 shows the morphology of the organoid cultured on Matrigel (FIG. 3A) or cellulose sponge (FIG. 3B).

FIG. 4 shows the morphology change of the organoid cultured on Matrigel or cellulose sponge through the culture periods.

FIG. 5 shows the distribution (FIG. 5A) and number (FIG. 5B) of organoid in cellulose sponge.

DETAIL DESCRIPTION OF THE INVENTION

Figure 1:
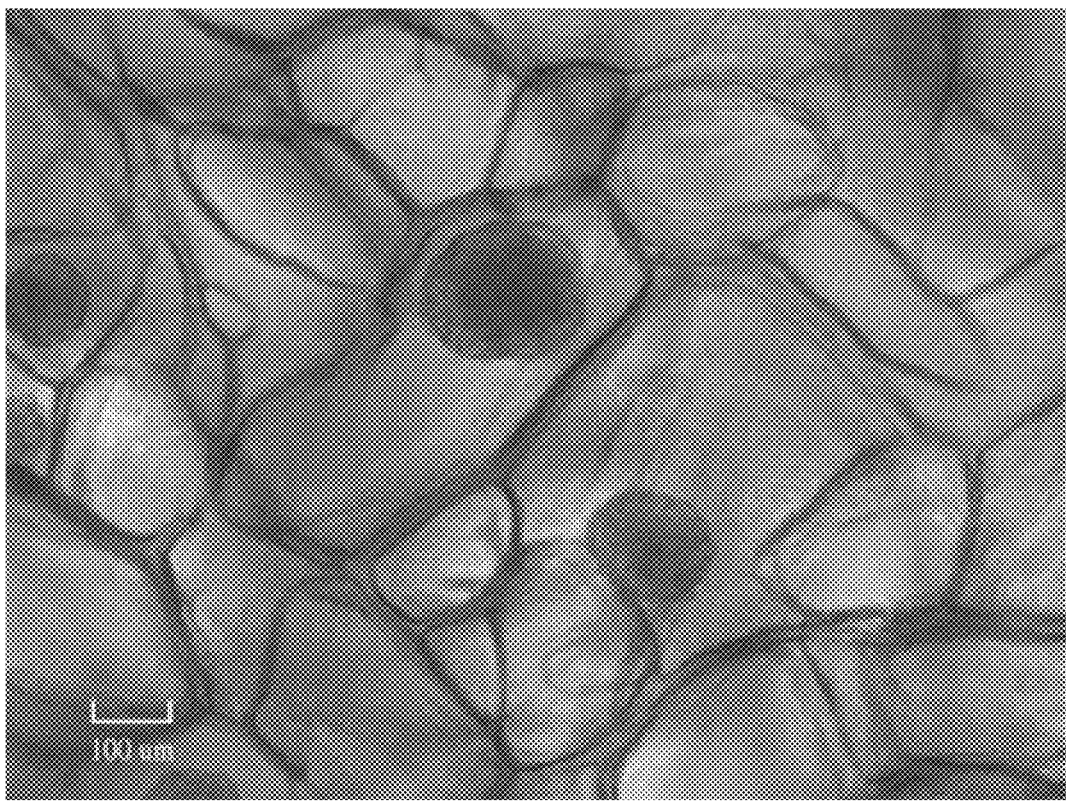
FIG. 1 is a magnified optical microscopy image of the cellulose sponge with additionally added alcohol of the present invention after cells being seeded.

Unless otherwise specified, "a" or "an" means "one or more".

The term "sponge" as used herein includes a three-dimensional structure of any shape, size, or composition, which can be used as a structure for attachment, adherence or implantation of at least one kind of cell and can serve the purpose of promoting normal cell growth and/or proliferation and/or differentiation. In one embodiment of the present invention, the sponge is made from cellulose. Since the cellulose sponge prepared by the method disclosed in the present invention are oriented for medical use, the cellulose sponge is preferably used in a biocompatible manner. In another embodiment of the present invention, the cellulose sponge prepared by the method disclosed in the present invention is used for cell culture and the cellulose sponge has high air permeability and nutrient permeability (i.e., a better specific surface area).

The term "initiator" as used herein indicates a kind of compound which is easily decomposed into free radicals by heat or light and triggers polymerization of monomers. It can be used to trigger free radical polymerization and copolymerization of the unsaturated chain of monomers. It also can be used in cross-linking reaction for unsaturated polymer.

An organoid is a miniaturized and simplified version of an organ produced in vitro in three dimensions that shows realistic micro-anatomy. They are derived from one or a few cells from a tissue, which can self-organize in three-dimensional culture.

The present invention provides a method for predicting an effect of a medication or a treatment regimen to a subject suffering from a cancer, the method comprises: (A) obtaining a tissue from the subject; (B) dissociating the tissue to obtain a multicellular cluster, wherein the multicellular cluster comprises the cancer cell; (C) culturing the multicellular cluster on a cellulose sponge; (D) exposing the cultured multicellular cluster to the medication or the treatment regimen; and (E) measuring a first survival rate of the cancer cell before exposing to the medication or the treatment regimen and a second survival rate of the cancer cell after exposing to the medication or the treatment regimen, when the second survival rate is lower than the first survival rate, the method predicts positive effect of the medication or the treatment regimen to the subject.

The present invention further provides a method for predicting an effect of a medication or a treatment regimen, the method comprises: (A) obtaining a tissue from a subject suffering from a disease; (B) dissociating the tissue to obtain a multicellular cluster, wherein the multicellular cluster comprises the diseased cells; (C) culturing the multicellular cluster on a cellulose sponge; (D) exposing the cultured multicellular cluster to the medication or the treatment regimen; and (E) measuring a first survival rate of the diseased cells before exposing to the medication or the treatment regimen and a second survival rate of the diseased cells after exposing to the medication or the treatment regimen, when the second survival rate is lower than the first survival rate, the method predicts positive effect of the medication or the treatment regimen to the subject.

According to the method of the present invention, in one preferred embodiment, the treatment regimen is chemotherapeutic agents. In a more preferred embodiment, the chemotherapeutic agents are Cisplatin and 5-Fluorouracil. In another embodiment, the cancer is colorectal cancer. In a preferred embodiment of the present invention, the cultured multicellular cluster forms an organoid.

According to one embodiment of the present invention, a method for preparing the cellulose sponge comprising: (A) providing a solution of hydroxypropyl cellulose having a self-crosslinkable substituent; and (B) irradiating the solution of hydroxypropyl cellulose having the self-crosslinkable substituent with γ-ray for crosslinking, wherein a method for preparing the hydroxypropyl cellulose having the self-crosslinkable substituent comprises: (a) dissolving hydroxypropyl cellulose in dimethylformamide to form a hydroxypropyl cellulose solution; (b) dissolving a compound comprising the self-crosslinkable substituent in dimethylformamide and slowly adding it drop by drop into the hydroxypropyl cellulose solution; (c) adding alcohol for reaction; and (d) reacting and drying at room temperature to form the hydroxypropyl cellulose having the self-crosslinkable substituent.

According to another embodiment of the present invention, a method for preparing the cellulose sponge comprising: (A) providing a solution of hydroxypropyl cellulose having a self-crosslinkable substituent; and (B) adding an initiator and a catalyst into the solution of hydroxypropyl cellulose having the self-crosslinkable substituent for crosslinking, wherein a method for preparing the hydroxypropyl cellulose having the self-crosslinkable substituent comprises: (a) dissolving hydroxypropyl cellulose in dimethylformamide to form a hydroxypropyl cellulose solution; (b) dissolving a compound comprising the self-crosslinkable substituent in dimethylformamide and slowly adding it drop by drop into the hydroxypropyl cellulose solution; (c) adding an alcohol for reaction; and (d) reacting and drying at room temperature to form the hydroxypropyl cellulose having the self-crosslinkable substituent.

According to the method for preparing the cellulose sponge, in one preferred embodiment, the compound comprising the self-crosslinkable substituent comprises but is not limited to allyl isocyanate, methacrylic acid, acrylic acid, or glycidyl methacrylate.

According to the method for preparing the cellulose sponge, in one preferred embodiment, the volume of the alcohol is 1.5-50% of the total volume of the dimethylformamide; in another preferred embodiment, the volume of the alcohol is 7.5-40% of the total volume of the dimethylformamide; in yet another preferred embodiment, the volume of the alcohol is 10-35% of the total volume of the dimethylformamide.

According to the method for preparing the cellulose sponge, in one preferred embodiment, the alcohol comprises but is not limited to methanol, ethanol, propanol or butanol.

According to the method for preparing the cellulose sponge, in one preferred embodiment, the initiator is persulfate initiator; and the catalyst is organic amine catalyst. In another preferred embodiment, the persulfate initiator comprises but is not limited to sodium persulfate, ammonium persulfate or potassium persulfate; and the organic amine catalyst comprises but is not limited to N,N,N',N'-tetramethylethylenediamine (TEMED), N,N,N',N'-tetrakis(2-hydroxypropyl)ethylenediamine (TKHED), N,N,N',N'-tetramethyl-3-(10H-phenothiazin-10-yl)-1,2-propanediamine, N,N,N',N'-tetramethylpregn-5-ene-3β,20α-diamine, N,N,N',N'-tetramethyl-1,4-butanediamine, 4,4'-tetramethyldiamino diphenylmethane, N,N,N',N'-tetramethyl-1,4-benzenediamine or N,N,N',N'-tetramethyl-1,4-napthalenediamine.

Examples

The examples below are non-limiting and are merely representative of various aspects and features of the present invention.

Preparation of Cellulose Sponge

Preparation of the cellulose sponge was divided into two steps:

1. Synthesis of Hydroxypropyl Cellulose Having a Substituent:

(1) Hydroxypropyl cellulose (HPC) ($M_n \approx 10,000$) was dehydrated by azeotropic distillation in toluene;

(2) 3.0 g dehydrated HPC was dissolved in 120 ml of dimethylformamide (DMF);

(3) 3.84 ml of allyl isocyanate was dissolved in 5 ml of dimethylformamide and then was slowly added drop by drop to the above prepared hydroxypropyl cellulose solution;
(4) 37.5 ml of alcohol (such as propanol) was added for reaction, the volume of the alcohol is 30% of the total volume of dimethylformamide (dimethylformamide 125 ml×30%=37.5 ml, the volume ratio of dimethylformamide: alcohol=3.3:1);
(5) One drop of dibutyltin dilaurate was added as a catalyst;
(6) Stirred at room temperature for 48 hours;
(7) The volume was reduced by using a rotatory evaporator and then the polymer was separated by ether; and
(8) The reaction products were collected by vacuum filtration and precipitated into diethyl ether; the residual impurities were removed by Soxhlet extraction from diethyl ether to form hydroxypropyl cellulose having the substituent.

2. Gamma ray irradiation:
(1) Hydroxypropyl cellulose having a substituent in dry form was formulated into a 10 wt % aqueous solution and placed in a glass tube (diameter 10 mm×height 50 mm);
(2) Temperature testing procedure: the aqueous solution changed from transparent into opalescent, a temperature controller was used to control the temperature, the sample stayed for a period of time at each temperature when the temperature was increased in order to observe color changes visually. When creamy-white color was observed but without the formation of layers and precipitations (indicating the formation of a stable colloidal system which was beneficial to subsequent formation of a three-dimensional porous structure), the corresponding temperature was recorded and the temperature ranged from 38~45° C. The recorded temperature would be used in subsequent gamma-ray irradiation for crosslinking.
(3) Irradiated with gamma ray at the above recorded temperatures; and
(4) The hydroxypropyl cellulose having the substituent solidified after irradiation, the finish product was obtained after washing and freeze-drying.

Alternatively, the cellulose sponge was also made by the following two steps:

1. Synthesis of hydroxypropyl cellulose having a substituent:
(1) Hydroxypropyl cellulose (HPC) ($M_n \approx 10,000$) was dehydrated by azeotropic distillation in toluene;
(2) 3.6 g dehydrated HPC was dissolved in 200 ml of dimethylformamide (DMF);
(3) 4.18 ml of allyl isocyanate was dissolved in 5 ml of dimethylformamide and then was slowly added drop by drop to the above prepared hydroxypropyl cellulose solution;
(4) 24.6 ml of alcohol (such as propanol) was added for reaction, the volume of the alcohol is 12% of the total volume of dimethylformamide (dimethylformamide 205 ml×12%=24.6 ml, the volume ratio of dimethylformamide: alcohol=8.3:1);
(5) One drop of dibutyltin dilaurate was added as a catalyst;
(6) Stirred at room temperature for 48 hours;
(7) The volume was reduced by using a rotatory evaporator and then the polymer was separated by ether; and
(8) The reaction products were collected by vacuum filtration and precipitated into diethyl ether; the residual impurities were removed by Soxhlet extraction from diethyl ether to form hydroxypropyl cellulose having the substituent.

Solidification Process:
(1) Hydroxypropyl cellulose having a substituent in dry form was formulated into a 10 wt % aqueous solution and placed in a glass tube (diameter 10 mm×height 50 mm);
(2) 1.2 g of ammonium persulfate (APS) and 35 µL of tetramethylethylenediamine (TEMED) were added into the solution under the condition of 2-8° C.;
(3) The glass tube was placed in low temperature (−20° C.) for the reaction for 24 hours; and
(4) The glass tube was moved to the room temperature for the reaction for 48 hours, the finish product was obtained after washing and freeze-drying.

The method for preparing the cellulose sponge without additionally added alcohol of the present invention was the same as described above, except that no alcohol was additionally added in step 1, i.e., step (4) of step 1 was skipped.

Applications of Cellulose Sponge

Cell culture conditions: HepG2 cells (human liver cancer cells), the culture medium was the high glucose Dulbecco's modified Eagle's medium (DMEM) supplemented with 10% fetal bovine serum, the cultivation conditions were 37° C. and 5% $CO_2$.

Steps for inoculating cells: The cellulose sponge was placed in a 48-well plate, cell concentration of HepG2 was adjusted to $5 \times 10^6$ cells/ml, 60 µL was taken to be inoculated in the cellulose sponge, and after being placed in an incubator for 4 hours the cellulose sponge was removed from the incubator and 500 µL of culture medium was added. Subsequently the cellulose sponge was washed with phosphate buffer saline solution every three days and the fresh culture medium was added.

Figure 2:
FIG. 2 is a magnified optical microscopy image of the cellulose sponge according to the present invention but without additionally added alcohol after cells being seeded.

FIG. 1 and FIG. 2 are images observed 24 hours after HepG2 were seeded, FIG. 1 is the cellulose sponge with additionally added alcohol; FIG. 2 is the cellulose sponge without additionally added alcohol. They are magnified images observed the next day after HepG2 were inoculated using an optical microscope. It was found that, with respect to the cellulose sponge with additionally added alcohol (FIG. 1), after the cells were inoculated the structure of the pore morphology was maintained and the cells were in a spheroid form, close to the actual pattern of the liver cells in human body. With respect to the cellulose sponge according to the present invention but without additionally added alcohol (FIG. 2), after cells were inoculated the structure of the pore morphology was not maintained, the pore size was significantly reduced, and the cells inclined to succumb to apoptosis. Therefore, it suggested that the pore morphology significantly affected the cell morphology.

Assessment of Clinical and In Vitro Response

The patient was a 60-year-old female with a clinical diagnosis of rectal cancer, wherein the TNM Classification of Malignant Tumors (TNM) was determined as T4N0M0 and the pathological diagnosis was adenocarcinoma stage II. The tumor tissue of the patient was cultured on a Matrigel or cellulose sponge to obtain the patient-derived organoid, PDO. The culture method was as follows:

1. The steps of dissociating the tumor tissue to obtain the tumor multicellular cluster:
   (1) take a soybean size tumor tissue from the said patient and wash the tumor tissue with phosphate buffer saline (PBS);
   (2) place the tumor tissue in a 24-well plate and add tumor lysis buffer;
   (3) cut the tumor tissue with sterile scissors;
   (4) supplement tumor lysis buffer, dissociate the tumor tissue at 37° C. for 2 hours;
   (5) filter the dissociation solution with 100-µm Nylon Filter;
   (6) centrifuge at 1500 rpm for 5 min and discard the supernatant;

(7) add about 3 mL red blood lysis buffer and resuspend the pellet for 5 min at room temperature;
(8) add about 10 mL PBS to dilute the suspension containing the red blood lysis buffer;
(9) centrifuge at 1500 rpm for 5 min and discard the supernatant;
(10) add about 8 mL PBS to wash the pellet and centrifuge at 1500 rpm for 5 min, discard the supernatant;
(11) add 1 mL PBS to resuspend the pellet;
(12) obtain the said tumor multicellular cluster.

2. The steps of cell culture:
(1) prepare the culture medium: advanced Dulbecco's modified Eagle's medium (DMEM)/F12 supplemented with bispecific antibodies, 10 mmol/L 4-(2-hydroxyethyl)-1-piperazineethanesulfonic acid (HEPES), GlutaMAX and 10% fetal bovine serum (FBS)
(2) place the cellulose sponge or Matrigel in a 48-well plate with tweezers;
(3) add 20 μL tumor single cell suspension buffer;
(4) incubate at 37° C. for 4 hours;
(5) add 300 μL culture medium and put it in the cell incubator (5% $CO_2$, 37° C.) to continue the culture;
(6) remove the culture medium every three days, rinse the culture with PBS, and add fresh culture medium;
(7) observe the results with an optical microscope on the third, seventh and eleventh days.

The organoid formed from the said patient's cancer tissue (including the cancerous cells and the corresponding paracancerous tissue) was established, passed on to the P2 generation (FIG. 3), and cryopreserved. The growing process of the patient-derived organoid, PDO, was observed with an optical microscope (FIG. 4). It was found that in the cellulose sponge, there was an increase in the size of the organoid overtime. Therefore, the environment of the cellulose sponge is benefit for the cell growth. In particular, said organoid was obtained by culturing in the Matrigel and the cellulose sponge, respectively. The cellulose sponge uses the plant-derived hydropropyl cellulose, which has the following advantages for organoid growth: (1) in contrast to the PDO obtained by culturing in the Matrigel ($PDO^{Matrigel}$), the PDO obtained by culturing in the cellulose sponge ($PDO^{cellusponge}$) has more uniform size (FIG. 3); (2) in contrast to $PDO^{Matrigel}$ the number of $PDO^{cellusponge}$ is more, which is mainly due to the differences in the spatial structures, wherein the Matrigel is hillock-shaped, and the organoid mainly grows in the center of the hill of the Matrigel, while the cellulose sponge is cylindrical with larger growth space and the organoid can grow more evenly and in more quantity in the cellulose sponge (FIG. 5); (3) the culturing method is economic and simple: in addition to R-spondin-1, epidermal growth factor (EGF), Noggin and Wnt 3a, the traditional $PDO^{Matrigel}$ culture medium also requires the addition of nicotinamide, small molecule inhibitors of Alk and inhibitors of p 38 (Jung, P. et al. Isolation and in vitro expansion of human colonic stem cells. *Nat Med* 17, 1225-1227 (2011)). In the present invention, it is demonstrated that the long-term culture of the said $PDO^{cellusponge}$ in the said cellulose sponge can be obtained without the addition of these three small molecule inhibitors. Furthermore, culturing of the said $PDO^{cellusponge}$ could avoid the tedious operation of the Matrigel culture.

Use CCK-8 assay as the survival rate test for PDO:
1. Place the said cellulose sponge in a 48-well plate with tweezers.
2. Add 20 μL tumor single cell suspension buffer.
3. Incubate at 37° C. for 4 hours.
4. Add 300 μL culture medium and continue the culture in the cell culture incubator (5% CO2, 37° C.).
5. Perform the CCK-8 assay for the cell survival rate test on the first, second, third and fourth day, respectively, wherein the combination of Cisplatin (CP) and 5-Fluorouracil (5-FU) was administered in the medication group and no administration in the control group.
6. Remove the culture medium at planned experiment time.
7. Add 200 μL fresh culture medium and 20 μL CCK-8 solution into each well.
8. Incubate at 37° C. for 1-4 hours.
9. Read the OD 450 nm values.

Figure 6:
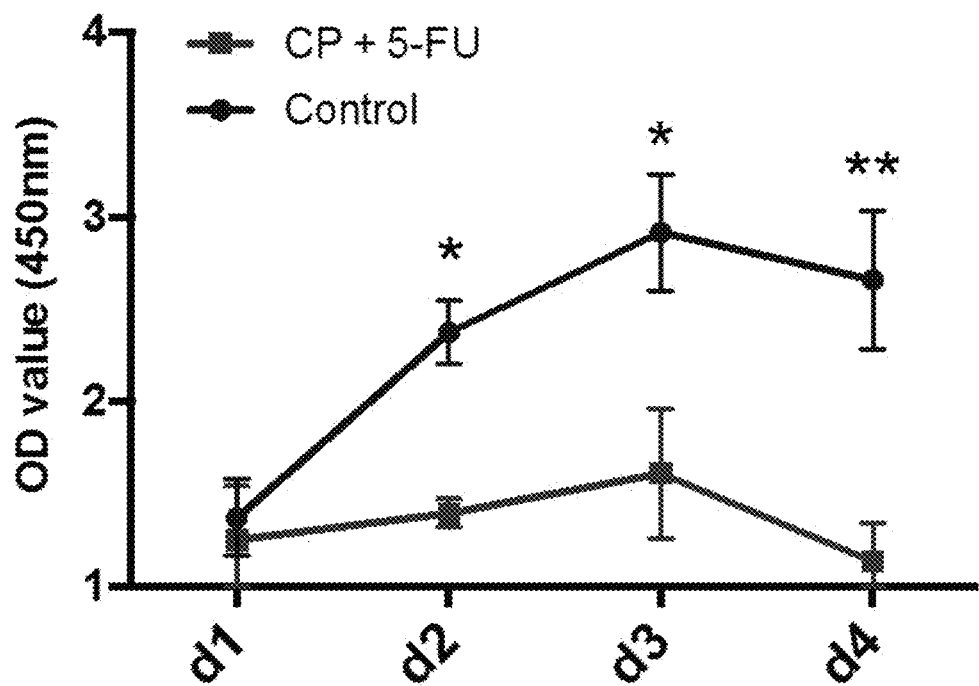
FIG. 6 shows the survival rate of the organoid before and after exposing to the medication.
Figure 7A:
FIG. 7 shows the computed tomography images of the patient before (FIG. 7A) and after (FIG. 7B) the chemotherapy.
Figure 7B:
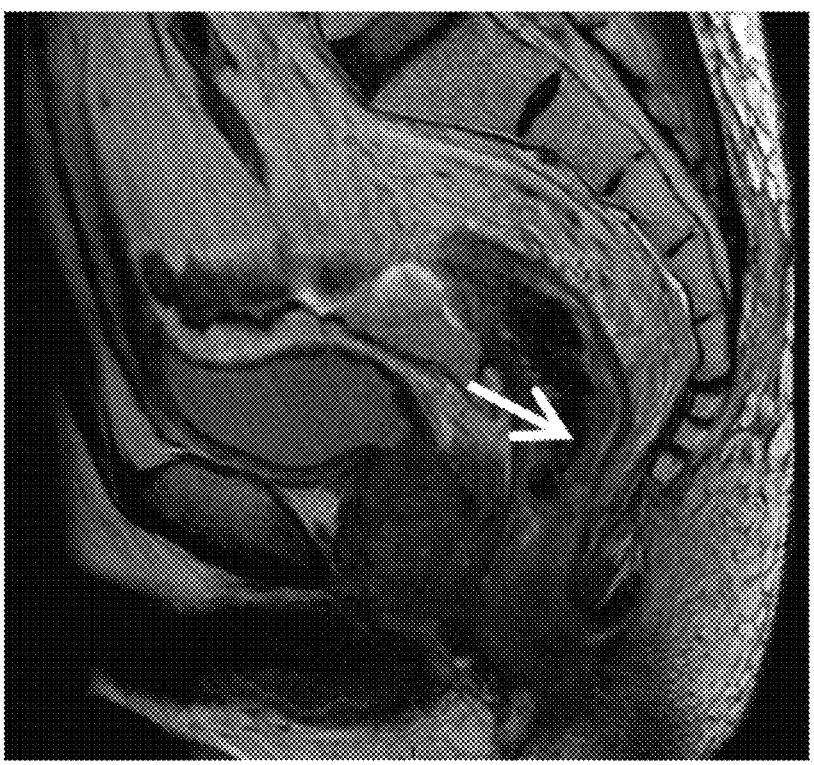

FIG. 6 shows that the survival rate declines significantly after the administration of the combination of Cisplatin and 5-fluorouracil, therefore the organoid is indicative before and after the administration of the medication. Subsequently, based on the results of CCK-8 assay, the medication was administered to said patient to perform the chemotherapy treatment regimen. The treatment regimen was XELOX, wherein the treatment course was as follows: (1) oxaliplatin was injected to the said patient on the first day while capecitabine was taken orally for two weeks; (2) the medication was discontinued for one week. The treatment course was lasted for three weeks, and the efficacy was assessed after two treatment courses. FIG. 7A and FIG. 7B show that the bright, white-gray tumor area (indicated by the arrow) reduced significantly, which is determined as the partial response (PR) of the tumor tissue, wherein the results is in agreement with the data obtained from the in vitro culture of the organoids. Consequently, it is believed that the cellulose sponge not only being suitable for the growth of the primary tumor cells, it can also be used in clinical medication test simulation; in addition, the doctor can determine the treatment regimen according to the simulation results of the patient to achieve the personalized medicine.

What is claimed is:

1. A method for predicting an effect of a medication or a treatment regimen, the method comprises:
(A) obtaining a tissue from a subject suffering from a disease;
(B) dissociating the tissue to obtain a multicellular cluster, wherein the multicellular cluster comprises the diseased cells;
(C) culturing the multicellular cluster on a cellulose sponge;
(D) exposing the cultured multicellular cluster to the medication or the treatment regimen; and
(E) measuring a first survival rate of the diseased cells before exposing to the medication or the treatment regimen and a second survival rate of the diseased cells after exposing to the medication or the treatment regimen,
when the second survival rate is lower than the first survival rate, the method predicts positive effect of the medication or the treatment regimen to the subject;
wherein the cellulose sponge of step (C) is prepared by a method comprising:
(i) dissolving hydroxypropyl cellulose in dimethylformamide to form a hydroxypropyl cellulose solution;
(ii) dissolving a compound comprising a self-crosslinkable substituent in dimethylformamide and slowly adding it drop by drop into the hydroxypropyl cellulose solution;
(iii) adding alcohol for forming a mixed solution comprising dimethylformamide, hydroxypropyl cellulose, the compound comprising the self-crosslinkable substituent and alcohol to stabilize the pore morphology of the cellulose sponge;

(iv) drying at room temperature to form a hydroxypropyl cellulose having the self-crosslinkable substituent;

(v) formulating the dried hydroxypropyl cellulose having the self-crosslinkable substituent into an aqueous solution; and (vi) irradiating the aqueous solution of hydroxypropyl cellulose having the self-crosslinkable substituent with γ-ray for crosslinking.

2. The method of claim 1, wherein the diseased cells are cancer cells.

3. The method of claim 1, wherein the medication or the treatment regimen is chemotherapeutic agents.

4. The method of claim 3, wherein the chemotherapeutic agents are Cisplatin or 5-Fluorouracil.

5. The method of claim 1, wherein the cultured multicellular cluster forms an organoid.

6. The method of claim 1, wherein the self-crosslinkable substituent comprises allyl isocyanate, methacrylic acid, acrylic acid, or glycidyl methacrylate.

* * * * *